United States Patent [19]

Dage et al.

[11] Patent Number: 4,552,880

[45] Date of Patent: Nov. 12, 1985

[54] AROYLIMIDAZOLONES

[75] Inventors: Richard C. Dage; Richard A. Schnettler, both of Cincinnati, Ohio

[73] Assignee: Merrell Dow Pharmaceuticals Inc., Cincinnati, Ohio

[21] Appl. No.: 562,758

[22] Filed: Dec. 21, 1983

Related U.S. Application Data

[63] Continuation-in-part of Ser. No. 466,409, Feb. 15, 1983, abandoned.

[51] Int. Cl.[4] .................. C07D 233/30; C07D 403/30; C07D 211/70; C07D 401/00

[52] U.S. Cl. .................................... 514/277; 514/392; 548/321; 548/318; 548/320; 546/351; 546/278

[58] Field of Search ........................ 548/321, 318, 320; 546/351, 278; 424/273 R, 263; 514/277, 392

[56] References Cited

U.S. PATENT DOCUMENTS 2,397,250 3/1946 Duschinsky ........................ 548/321

*Primary Examiner*—Henry R. Jiles
*Assistant Examiner*—Robert C. Whittenbaugh
*Attorney, Agent, or Firm*—Raymond A. McDonald; Gary D. Street; Stephen L. Nesbitt

[57] ABSTRACT

This invention relates to certain substituted aroylimidazolones, their acid and base addition salts thereof, and to their use as cardiotonic agents.

13 Claims, No Drawings

AROYLIMIDAZOLONES

This is a continuation-in-part application of application Ser. No. 466,409, filed Feb. 15, 1983 now abandoned.

This invention relates to pharmaceutically active 1,3-dihydro-2H-imidazole-2-ones of the formula:

Formula 1

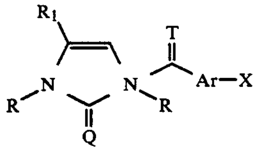

and the pharmaceutically acceptable salts thereof, wherein Q and T are each an oxygen atom or a divalent sulfur atom; R is hydrogen, lower alkyl, lower alkanoyl or benzoyl; $R_1$ is hydrogen or lower alkyl; Ar is pyridyl, phenyl, pyrryl, thienyl or furanyl; and X is a substituent of the group cyano, carboxy, carboxamido, alkoxycarbonyl, amidino and imidazol-2-yl- and the acid base addition salts thereof. These compounds are useful as cardiotonics in the treatment of cardiac failure.

As used herein, the term "lower alkyl" includes straight or branched-chain alkyl radicals of from 1 to 4 carbon atoms, e.g., methyl, ethyl, propyl, isopropyl, n-butyl, isobutyl and t-butyl, with methyl and ethyl being preferred. The term "lower alkanoyl" includes straight and branched-chain alkanoyl groups of from 2 to 4 carbon atoms such as acetyl, propionyl, n-butyryl and isobutyryl. The term "pyridyl" includes 2-, 3- and 4-pyridyl; "furanyl" includes 2- and 3-furanyl; "thienyl" includes 2- and 3-thienyl and "pyrryl" includes 2- and 3-(1H-)pyrryl). The "X" substituent attached to the foregoing "Ar" moieties include cyano (—C≡N), carboxamide (—$CONR_1R_1$), carboxyl (—COOH), alkoxycarbonyl, lower alkanoyl (—CO lower alkyl), (—COO lower alkyl), amidino

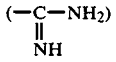

and imidazol-b 2-yl

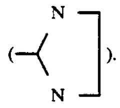

$R_1$ is hydrogen or lower alkyl.

Those compounds of Formula 1 wherein R is hydrogen are acidic and may form pharmaceutically active base addition salts of Formula 2:

wherein Ar-X, Q, T and $R_1$ are defined in Formula 1, and M is a pharmaceutically acceptable alkali metal ion such as sodium or potassium ion; alkaline earth metal ion such as calcium or magnesium ion, transition metal ion such as zinc or iron ion or main group metal ion such as aluminum ion. In general, the pharmaceutically acceptable base addition salts are crystalline materials which are more soluble in water and various hydrophilic solvents and which in comparison to their free acid forms, generally demonstrate higher melting points.

The compounds of Formula 1 wherein Ar-X is pyridyl may form pharmaceutically active acid addition salts with both inorganic and organic acids. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Such salts can exist in either a hydrated or a substantially anhydrous form. In general, the acid addition salts of these compounds are crystalline materials which are soluble in water and various hydrophilic organic solvents and which in comparison to their free base forms generally demonstrate higher melting points and an increased chemical stability.

It is apparent from the above general Formula 1 that the compounds of this invention are 1,3-dihydro-4-X-picolinoyl-2H-imidazole-2-ones, 1,3-dihydro-4-X-nicotinoyl-2H-imidazole-2-ones, 1,3-dihydro-4-X-isonicotinoyl-2H-imidazole-2-ones, 1,3-dihydro-4-X-benzoyl-2H-imidazole-2-ones, 1,3-dihydro-4-X-thienoyl-2H-imidazole-2-ones, 1,3-dihydro-4-X-furanoyl-2H-imidazole-2-ones and 1,3-dihydro-4-X-pyrroyl-2H-imidazole-2-ones.

The preferred compounds of this invention are those wherein Q and T are each oxygen. Of these, preferred compounds are those wherein Ar is pyridyl or phenyl with the 4- and 2-position isomers of pyridyl being preferred. Most preferred are 4-pyridyl and phenyl. Of these, the preferred compounds are those wherein R is hydrogen and $R_1$ is H, methyl or ethyl with ethyl being most preferred. The preferred X-substituents for these compounds are cyano, carboxamido and carboxy.

In general, the compounds of this invention are prepared by standard techniques analogously known in the art. A preferred synthesis for preparing compounds of this invention conveniently involves the reaction of an aminodiketone of Formula 3 with either a cyanate or thiocyanate salt, preferably using the sodium or potas- Formula 2

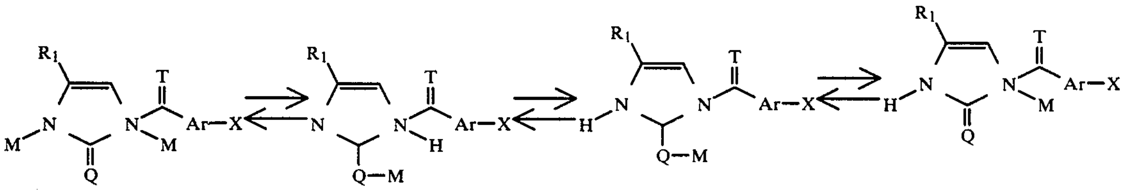

sium cyanate or thiocyanate, to produce a desired 1,3-dihydro-4-(X'-Ar)-5-$R_1$-2H-imidazole-2-one (or 2-thione). This reaction may be depicted as follows:

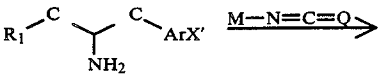

3

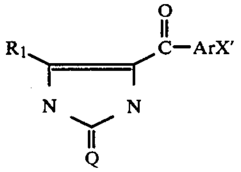

4 wherein X' is cyano, $R_1$, Ar and Q are as previously defined and M is a metal, preferably potassium or sodium. This reaction is performed by mixing about 1 molar equivalent of the appropriate aminodiketone with about 1 to about 5 molar equivalents, preferably about 1 molar equivalent of a cyanate or thiocyanate salt in a suitable solvent. The reaction is allowed to proceed for about 5 minutes to about 10 hours depending on the reactants, the solvent and the temperature which can be from about 0° C. to about 100° C., preferably about 80° C. Suitable solvents for this reaction are any non-reactive solvents such as water or water miscible solvent, for example, an organic acid such as acetic acid; an alcohol such as methanol or ethanol; or an ether such as tetrahydrofuran or p-dioxan. Preferably any non-aqueous solvent is mixed with water. The preferred solvent is water.

The product of this reaction may be isolated by any art-known procedure such as by conversion to the corresponding sodium or potassium salt and reprecipitation with carbon dioxide or a mineral acid such as dilute hydrochloric acid.

In those instances wherein "X'" is other than a cyano moiety, their preparation can readily by achieved from the compounds of Formula 4 by standard techniques. For example, the cyano moiety may be converted to a carboxyl moiety by hydrolyzing the nitrile with 6N hydrochloric acid, sulfuric and/or other mineral acids under standard conditions such as by heating at reflux temperatures for about 12–24 hours. The carboxyl moiety may be converted to an alkoxycarbonyl moiety by the standard Fisher esterification procedure such as by heating the carboxy-containing compounds with an appropriate alcohol in the presence of an acid, e.g., 3% hydrochloric acid. The carboxamido-containing compounds may be prepared by converting the alkoxycarbonyl moiety by heating the esters in the presence of ammonia or an appropriate amine, preferably in a pressure bomb at about 100°–150° C. in an inert solvent, e.g., benzene, toluene and the like. Alternatively, the carboxamido moiety may be prepared by hydrolyzing a nitrile with concentrated sulfuric acid by heating on a steam bath at temperatures of about 50°–100° C.

In those instances wherein X is imidazol-2-yl, such compounds are prepared by a condensation reaction wherein the nitrile is heated to from about 150°–200° C. with ethylene diamine for about 2 hours. The amidino compounds are prepared from corresponding nitriles wherein the nitrile is converted to an imino ether which is converted to the amidino moiety by treating the imino ether with ammonia in alcohol at temperatures of about 0° C. room temperature.

The compounds of Formula 1 wherein Q and T are each oxygen atoms and wherein R is hydrogen may also be prepared by a Friedel-Crafts acylation of 1,3-dihydro-2H-imidazole-2-one of Formula 5:

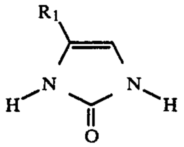

Formula 5 wherein $R_1$ is as defined in Formula 1. The acylating agent may be an aroyl halide, or an X-substituted aroyl halide, particularly a cyano substituted aroyl halide, i.e., pyridoyl chlorides, benzoyl chlorides, furanoyl chlorides, thienoyl chlorides or pyrroyl chlorides with or without a cyano group attached thereto.

The Friedel-Crafts reactions of this invention are performed by premixing about 1 molar equivalent of the appropriate imidazole-2-one with about 1 molar equivalent to about 10 molar equivalents, preferably about 3 to 6 molar equivalents, of a Lewis acid catalyst in a suitable solvent, for example, petroleum ethers; a chlorinated hydrocarbon, such as carbon tetrachloride, ethylene chloride, 1,1,2,2,-tetrachloroethane, methylene chloride or chloroform; a chlorinated aromatic, such as 1,2,4-trichlorobenzene or o-dichlorobenzene; carbon disulfide; or nitrobenzene. The preferred solvent is 1,1,2,2-tetrachloroethane (tetrachloroethane). About 1 molar equivalent to about 10 molar equivalents, preferably about 1 molar equivalent of the appropriate aroyl compound is added, preferably dropwise, to the mixture of imidazole-2-one, Lewis acid, and solvent and the reaction is allowed to proceed for about ½ hour to about 10 hours, preferably from about 1 hour to about 5 hours depending on the reactants, the solvent, and the temperature which can be from about −78° C. to about 150° C., preferably about 0° to about 100° C., most preferably about 85° C. The resulting aroyl imidazole-2-one may be isolated from the reaction mixture by any suitable art-known procedure, preferably by quenching the reaction mixture with ice water or water followed by neutralization with aqueous sodium bicarbonate or other weak base and subsequently removing the product by filtration or extraction with organic solvents; typically ethanol, followed by solvent removal. Purification is typically by chromatography on silica gel or by standard recrystallization procedures.

Lewis acid catalysts suitable for use in the Friedel-Crafts reactions described herein are, for example, a Bronstead acid, such as a phosphoric acid, sulfuric acid, halogen substituted acetic acids, such as chloroacetic or trifluoroacetic acids, or a metallic halide, such as a boron halide, zinc chloride, zinc bromide, copper chloride, iron(III) bromide, iron(III) chloride, mercury(II) chloride, mercury(I) chloride, antimony bromide, antimony chloride, titanium(IV) bromide, titanium(IV) chloride, titanium(III) chloride, aluminum bromide or preferably aluminum chloride, phosphorous trichloride and phosphorous pentachloride.

When it is desired that T be a divalent sulfur atom, the corresponding aroylimidazole-2-one of Formula 1 (or 4) wherein T is an oxygen atom is reacted with phosphorus pentasulfide, $P_2S_5$, by procedures generally known in the art. This reaction may be performed by mixing about 1 molar equivalent of the aroylimidazole-2-one wherein T is an oxygen atom, with about 1 to about 5 molar equivalents, preferably about 1 molar equivalent, of $P_2S_5$, together with a suitable solvent. This reaction is allowed to proceed for about 1 to about 10 hours, preferably about 5 hours, depending on the reactant, the solvent and the temperature which can be from about 25° C. to about 125° C., preferably about 80° C. A suitable solvent for this reaction is any non-reactive solvent, for example, tetrahydrofuran, p-dioxan, benzene, toluene or pyridine. The preferred solvent is toluene.

When desired, one or both of the nitrogen atoms of the imidazole-2-one or imidazole-2-thione ring may be substituted with an alkyl group by any art-known procedure. Such methods include reacting the appropriate compounds of Formula 1 wherein R is hydrogen with a base and an alkylating agent in the presence of an unreactive solvent. Suitable bases for this reaction can be, for example, a hydride such as sodium hydride or calcium hydride or an alkoxide such as sodium ethoxide. Suitable alkylating agents for this reaction are, for example, an alkyl halide such as methyl iodide or a dialkylsulfate such as dimethylsulfate. Suitable unreactive solvents are, for example, dimethylformamide (DMF) or dimethylsulfoxide (DMSO). The reaction is allowed to proceed from about 1 minute to about 10 hours and the temperature may be from about 0° C. to about 100° C., preferably about 25° C. When it is desired that only one of the imidazole-2-one nitrogen atoms be substituted with an alkyl group, the appropriate aroylimidazole-2-one is reacted with from about 1 molar equivalent to about 10 molar equivalents of a base, preferably about 1 molar equivalent and with about 1 molar equivalent of an alkylating agent. Utilizing this procedure, both possible monoalkylated nitrogen isomers result. These isomers are separable by conventional art-known procedures such as fractional crystallization, fractional distillation or chromatography. When it is desired that both nitrogen atoms of the imidazole-2-one (or 2-thione) ring be alkyl substituted, the appropriate imidazole-2-one (or 2-thione) is reacted with from about 2 molar equivalents to about 10 molar equivalents of a base, preferably about 2 molar equivalents and from about 2 molar equivalents to about 10 molar equivalents of an alkylating agent, preferably about 2 molar equivalents.

When desired, the nitrogen atoms of the imidazole-2-one or the imidazole-2-thione may be substituted with an alkanoyl or benzoyl group by any suitable art-known procedure. Such methods include reacting an imidazole-2-one (or 2-thione) of Formula 1 wherein R is hydrogen with an acyl halide, preferably an acyl chloride such as acetyl chloride, n-propanoyl chloride, isopropanoyl chloride or benzoyl chloride. Normally, acylating reactions utilizing acyl halides employ an acid sponge such as triethylamine or pyridine to remove any hydrohalide as it is formed. Furthermore, the corresponding acid anhydride may be employed instead of the acyl halides. Acylation reactions are generally run without added solvent but may be performed using any nonreactive solvent, for example, petroleum ethers; chlorinated hydrocarbons such as chloroform, methylene chloride or carbon tetrachloride; carbon disulfide; ethereal solvents, such as diethylether, tetrahydrofuran or p-dioxan or aromatic solvents such as benzene, toluene or xylene. The reactions are allowed to proceed for about 1 hour to about 20 hours, preferably about 5 hours and the temperature may be from about 0° C. to about 200° C., preferably about 135°.

The alkali metal, alkaline earth metal, transition metal or main group metal base addition salts of the imidazole-2-ones (or the imidazole-2-thiones) of this invention may be prepared from a corresponding metal salt, for example, an alkoxide, such as sodium methoxide or potassium ethoxide, or a hydride such as calcium hydride. These reactions may be performed with or without a solvent. Suitable solvents are, for example, lower alcohols such as methanol, ethanol, isopropanol, n-propanol or n-butanol; or dimethylformamide (DMF). The imidazole-2-one and base are allowed to react for about 1 minute to about 24 hours, preferably about 1 hour, depending on the reactants and the temperature which can be from about −78° to about 150° C., preferably from about 0° to about 25° C.

The acid addition salts of the compounds of Formula 1 wherein Ar is pyridyl may be prepared by conventional procedures such as by treating a compound of Formula 1 with a suitable inorganic or organic acid. For example, 1-10 molar equivalents of acid is added to 1 molar equivalent of a compound of Formula 1 at a temperature of from −5° to 80° C., typically room temperature, and the reaction allowed to proceed from 0.1 to 5 hours. These reactions may be performed with or without added solvent. Suitable solvents are, for example, lower alcohols such as methanol, ethanol, isopropanol, n-propanol or n-butanol; or water, and ketones such as acetone, methyl ethyl ketone.

The aminodiketones of Formula 3 may be prepared by reduction of the appropriate oxime of Formula 6:

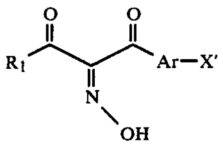

Formula 6 wherein $R_1$ and Ar-X' are as defined above in Formula 4. These oximes are reduced by any suitable method generally known in the art such as catalytically in acidic alcoholic medium such as ethanol-hydrochloric acid over an appropriate noble metal catalyst such as palladium on charcoal or with zinc or tin in acetic acid/acetic anhydride solution.

The oximes of Formula 6 may be prepared by any suitable art-known procedure such as nitrosation of the appropriate diketone of Formula 7, such as, for example, an aqueous solution of sodium nitrite added to an acetic acid solution of a compound of formula 7 at about 0° C. for about 1 to 5 hours.

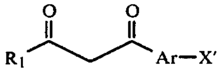

Formula 7

EXAMPLE 1

4-(4-Cyanobenzoyl)-5-ethyl-1,3-dihydro-2H-imidazol-2-one

To a stirred mixture of 3.38 grams (0.03 mole) of 1,3-dihydro-4-ethyl-2H-imidazol-2-one, 13.3 grams (0.1 mole) of anhydrous aluminum chloride and 50 ml of nitrobenzene is added 5.0 grams (0.03 mole) of 4-cyanobenzoyl chloride. The mixture is stirred at 80° C. for 6 hours, then poured on 500 grams of ice. The resulting precipitate is washed with diethyl ether and water and is recrystallized from 500 ml ethyl alcohol to give 4.76 grams of the title compound. M.P. 269–271° C.

In a similar manner, by substituting equivalent amounts of:
2-cyanoisonicotinoyl chloride,
3-cyanoisonicotinoyl chloride,
2-cyanonicotinoyl chloride,
5-cyanopicolinoyl chloride,
3-cyanopicolinoyl chloride,
6-cyanopicolinoyl chloride,
5-cyano-3-thienoyl chloride,
5-cyano-2-thienoyl chloride,
2-cyano-3-thienoyl chloride,
3-cyano-2-pyrroyl chloride,
2-cyano-3-pyrroyl chloride,
5-cyano-2-furanoyl chloride,
5-cyano-3-furanoyl chloride,
for the 4-cyanobenzoyl chloride of this example and by substantially following the process of this example there is produced the following compounds:
4-(2-cyanoisonicotinoyl)-5-ethyl-1,3-dihydro-2H-imidazol-2-one,
4-(3-cyanoisonicotinoyl)-5-ethyl-1,3-dihydro-2H-imidazol-2-one,
4-(2-cyanonicotinoyl)-5-ethyl-1,3-dihydro-2H-imidazol-2-one,
4-(5-cyanopicolinoyl)-5-ethyl-1,3-dihydro-2H-imidazol-2-one,
4-(3-cyanopicolinoyl)-5-ethyl-1,3-dihydro-2H-imidazol-2-one,
4-(6-cyanopicolinoyl)-5-ethyl-1,3-dihydro-2H-imidazol-2-one,
4-(5-cyano-3-thienoyl)-5-ethyl-1,3-dihydro-2H-imidazol-2-one,
4-(5-cyano-2-thienoyl)-5-ethyl-1,3-dihydro-2H-imidazol-2-one,
4-(2-cyano-3-thienoyl)-5-ethyl-1,3-dihydro-2H-imidazol-2-one,
4-(3-cyano-2-pyrroyl)-5-ethyl-1,3-dihydro-2H-imidazol-2-one,
4-(2-cyano-3-pyrroyl)-5-ethyl-1,3-dihydro-2H-imidazol-2-one,
4-(5-cyano-2-furanoyl)-5-ethyl-1,3-dihydro-2H-imidazol-2-one,
4-(5-cyano-3-furanoyl)-5-ethyl-1,3-dihydro-2H-imidazol-2-one.

Similarly, by substituting the 1,3-dihydro-4-ethyl-2H-imidazol-2-one reactant with 1,3-dihydro-4-methyl-2H-imidazol-2-one, 1,3-dihydro-2H-imidazol-2-one, or 1,3-dihydro-4-ethyl-2H-imidazol-2-thione and by substantially following the procedure of this example with the foregoing enumerated reactants there are produced the appropriately cyano-substituted 1,3-dihydro-2H-imidazol-2-ones and 1,3-dihydro-2H-imidazol-2-thiones.

EXAMPLE 2

4-[(5-Cyano-2-thienyl)carbonyl]-5-methyl-1,3-dihydro-2H-imidazol-2-one

A stirred mixture of 4-[(5-bromo-2-thienyl)carbonyl]-5-methyl-1,3-dihydro-2H-imidazol-2-one (10 grams, 0.034 mole), cuprous cyanide (3.0 grams, 0.034 mole) and dimethylformamide (150 ml) are refluxed for 4 hours. The resulting mixture is poured into a solution of 200 grams ferric chloride and 50 ml concentrated hydrochloric acid in 300 ml water. After the reaction mixture is maintained at 60°–70° C. for 20 minutes, the layers were separated. The aqueous layer is extracted with toluene and the combined organic layers are washed with water and dried. Evaporation of solvent gives the title compound which is recrystallized from methanol.

EXAMPLE 3

4-(4-Carboxybenzoyl)-5-propyl-1,3-dihydro-2H-imidazol-2-one

To 100 ml 6N hydrochloric acid is added 5.0 grams (0.019 mole) of 4-(4-cyanobenzoyl)-5-propyl-1,3-dihydro-2H-imidazol-2-one. The mixture is stirred and refluxed for 20 hours. Evaporation of solvent affords the title compound.

In a similar manner by using equivalent amounts of the appropriately substituted reactants in place of the 4-(4-cyanobenzoyl)-5-propyl-1,3-dihydro-2H-imidazol-2-one and by substantially following the procedure of this example there are produced:
4-(4-carboxybenzoyl)-5-methyl-1,3-dihydro-2H-imidazol-2-one,
4-(2-carboxyisonicotinoyl)-5-ethyl-1,3-dihydro-2H-imidazol-2-one,
4-(3-carboxyisonicotinoyl)-5-ethyl-1,3-dihydro-2H-imidazol-2-one,
4-(5-carboxypicolinoyl)-5-ethyl-1,3-dihydro-2H-imidazol-2-one,
4-(3-carboxy-2-pyrroyl)-5-ethyl-1,3-dihydro-2H-imidazol-2-one,
4-(5-carboxy-2-furanoyl)-5-ethyl-1,3-dihydro-2H-imidazol-2-one,
and the like.

EXAMPLE 4

4-(4-Carboethoxybenzoyl)-5-ethyl-1,3-dihydro-2H-imidazol-2-one

In 500 ml absolute alcohol is dissolved 5 grams 4-(4-carboxybenzoyl)-5-ethyl-1,3-dihydro-2H-imidazol-2-one. The mixture is stirred and refluxed while a slow stream of dry hydrogen chloride is introduced. The reaction is allowed to proceed for 7 hours after which the solvent is evaporated and the residue is recrystallized from alcohol to give the title compound.

In a similar manner by substituting equivalent amounts of the appropriate reactant (i.e., products of Example 3) for the 4-(4-carboxybenzoyl)-5-ethyl-1,3-dihydro-2H-2-one and by substantially following the process of this example there are produced:
4-(4-carboethoxybenzoyl)-5-methyl-1,3-dihydro-2H-imidazol-2H-2-one,
4-(2-carboethoxyisonicotinoyl)-5-ethyl-1,3-dihydro-2H-imidazol-2H-2-one,
4-(3-carboethoxyisonicotinoyl)-5-ethyl-1,3-dihydro-2H-imidazol-2H-2-one,
4-(5-carboethoxypicolinoyl)-5-ethyl-1,3-dihydro-2H-imidazol-2H-2-one,
4-(3-carboethoxy-2-pyrroyl)-5-ethyl-1,3-dihydro-2H-imidazol-2H-2-one,
4-(5-carboethoxy-2-furanoyl)-5-ethyl-1,3-dihydro-2H-imidazol-2H-2-one, and the like.

EXAMPLE 5

4-(4-Carboxamidobenzoyl)-5-methyl-1,3-dihydro-2H-imidazol-2-one

To 100 grams of concentrated sulfuric acid is added 10 grams (0.044 mole) of 4-(4-cyanobenzoyl)-5-methyl- 1,3-dihydro-2H-imidazol-2-one. The mixture is stirred at 60° C. for 5 hours, cooled and then poured on 1 kg ice. The resulting solid is collected, washed with water and recrystallized from ethanol to give the title compound.

In a similar manner, by substituting equivalent amounts of the appropriate reactants (i.e., products of the process of Example 1) for the 4-(4-cyanobenzoyl)-5-methyl-1,3-dehydro-2H-imidazol-2-one and by substantially following the process of this example there are produced:

4-(4-carboxamidobenzoyl)-5-ethyl-1,3-dihydro-2H-imidazol-2-one,
4-(2-carboxamidoisonicotinoyl)-5-ethyl-1,3-dihydro-2H-imidazol-2-one,
4-(3-carboxamidoisonicotinoyl)-5-ethyl-1,3-dihydro-2H-imidazol-2-one,
4-(5-carboxamidopicolinoyl)-5-ethyl-1,3-dihydro-2H-imidazol-2-one,
4-(3-carboxamido-2-pyrroyl)-5-ethyl-1,3-dihydro-2H-imidazol-2-one,
4-(5-carboxamido-2-furanoyl)-5-ethyl-1,3-dihydro-2H-imidazol-2-one, and the like.

EXAMPLE 6

4-(4-Amidinobenzoyl)-5-methyl-1,3-dihydro-2H-imidazol-2-one

A stream of dry hydrogen chloride is passed into a solution of 5 grams (0.022 mole) of 4-(4-cyanobenzoyl)-5-methyl-1,3-dihydro-2H-imidazol-2-one and 500 ml absolute ethanol until the solution is saturated. The solution is well stirred and kept at 0° C. with an ice salt bath. A solid forms which is collected and dried. This solid is suspended in 500 ml absolute ethanol and treated with 500 ml 9% ammonia in alcohol. Stirring is continued for 5 hours and ammonium chloride crystals are filtered from the reaction mixture. Evaporation of the filtrate affords the title compound.

Similarly by substituting equivalent amounts of the appropriate reactants (i.e., those compounds producible by Example 1) for the 4-(4-cyanobenzoyl)-5-methyl-1,3-dihydro-2H-2-one and by substantially following the process of this example there are produced:

4-(4-amidinobenzoyl)-5-ethyl-1,3-dihydro-2H-imidazol-2-one,
4-(2-amidinoisonicotinoyl)-5-ethyl-1,3-dihydro-2H-imidazol-2-one,
4-(3-amidinoisonicotinoyl)-5-ethyl-1,3-dihydro-2H-imidazol-2-one,
4-(5-amidinopicolinoyl)-5-ethyl-1,3-dihydro-2H-imidazol-2-one,
4-(5-amidino-2-pyrroyl)-5-ethyl-1,3-dihydro-2H-imidazol-2-one,
4-(5-amidino-2-furanoyl)-5-ethyl-1,3-dihydro-2H-imidazol-2-one, and the like.

EXAMPLE 7

4-[4-(3,4-Dihydro-1H-imidazol-2yl)benzoyl]-1,3-dihydro-5-ethyl-2H-imidazol-2-one A mixture of 5 grams (0.022 mole) of 4-(4-cyanobenzoyl)-5-ethyl-1,3-dihydro-2H-imidazol-2-one and 10 ml of methanol in 100 ml of tetrahydrofuran at 5° C. is treated with anhydrous HCl until saturated. The mixture is kept at 5° C. for 22 hours. The crude imino ether hydrochloride obtained is added to an ice-cooled mixture of 3.15 grams (0.03 mole) of aminoacetaldehyde dimethyl acetal and 10 ml methanol and refluxed 19 hours, concentrated under reduced pressure to give the amidine hydrochloride. Treatment of the amidine hydrochloride with concentrated $H_2SO_4$ gives the title compound.

Similarly by substituting equivalent amounts of the appropriate reactants (i.e., those compounds producible by the process of Example 1) for the 4-(4-cyanobenzoyl)-5-ethyl-1,3-dihydro-2H-imidazol-2-one and by substantially following the process of this example there are produced the corresponding 4-[4-(3,4-dihydro-1H-imidazol-2-yl)-aroyl]-5-alkyl-1,3-dihydro-2H-imidazol-2-one.

EXAMPLE 8

4-(4-Cyanothiobenzoyl)-5-ethyl-1,3-dihydro-2H-imidazol-2-one

Suspend 10 g of 4-(4-cyanobenzoyl)-5-ethyl-1,3-dihydro-2H-imidazol-2-one in 100 ml of toluene and add 20 g of phosphorous pentasulfide. Reflux the mixture for 6 hours and evaporate the solvent to yield the title compound.

Similarly, those products produced by the process of examples 1–7 may be converted to the corresponding thioisonicotinoyl, thionicotinoyl, thiopicolinoyl, thiothienoyl, thiopyrroyl and thiofuranoyl compounds by the procedures of this example.

EXAMPLE 9

1,3-dehydro-4-methyl-5-(4-cyanobenzoyl)-2H-imidazol-2-thione

To 9.8 g of 2-amino-1-(4-cyanophenyl)-1,3-butadione in 200 ml of 1N HCl is added 14.5 g of potassium thiocyanate, and the resulting solution is warmed on a steam bath for 30 minutes and then cooled. The title compound is re-crystallized from alcohol.

EXAMPLE 10

1,3-Dihydro-4-ethyl-5-(4-cyanothiobenzoyl)-2H-imidazol-2-thione

Ten g of 1,3-dihydro-4-ethyl-5-(4-cyanobenzoyl)-2H-imidazol-2-thione in toluene and phosphorous pentasulfide is heated at reflux temperature for 5 hours. Evaporation of the solvent provides the title compound.

Preparation of the thio analogs of the compounds preparable by the process of examples 1–7 may similarly be effected by the use of the procedures of examples 8–10.

The compounds of general Formula 1 may be used in the treatment of cardiac failure including congestive heart failure, backward heart failure, forward heart failure, left ventricular heart failure, or right ventricular heart failure or in the treatment of any other condition which requires the strengthening of heart action with a cardiotonic.

The utility of Formula 1 compounds as cardiotonics may be determined by administering the test compound (0.01–10 mg/kg) intravenously, intraperitoneally, intraduodenally or intragastrically in a suitable vehicle to a mongrel dog (either sex). The test dogs are anesthetized and prepared by isolating a suitable artery (e.g., femoral or common carotid) and vein (e.g., femoral or external jugular) introducing polyethylene catheters filled with 0.1% Heparin-Na to record arterial blood pressure and administer compounds, respectively. The chest is opened by splitting the sternum at the midline or by an incision at the left fifth intercostal space, and a pericardial cradle is formed to support the heart. A Walton-Brodie strain gage is sutured to the right or left ventricle to monitor myocardial contractile force. An electromagnetic flow probe may be placed around the root of the ascending aorta for measuring cardiac output less coronary blood flow. Heart failure is induced by administering sodium pentobarbital (20 to 40 mg/kg) followed by a continuous infusion of 1-2 mg/kg/min. or propranalol hydrochloride (4 mg/kg) followed by a continuous infusion of 0.18 mg/kg/min. to the blood perfusing the heart. Following administration of either of these cardiac depressants, the right atrial pressure dramatically increases and cardiac output is severely depressed. Reversal of these effects by the test compound indicates cardiotonic activity.

The compounds may be administered in various manners to achieve the desired effect. The compounds may be administered alone or in the form of pharmaceutical preparations to the patient being treated either orally or parenterally, that is, intravenously or intramuscularly. The amount of compound administered will vary with the patient, the severity of the cardiac failure and the mode of administration.

For oral or parenteral administration the cardiotonically effective amount of compound is from about 0.01 mg/kg of patients body weight per day up to about 500 mg/kg of patient body weight per day and preferably from about 0.10 mg/kg of patient body weight per day up to about 200 mg/kg of patient body weight per day.

For oral administration a unit dosage may contain, for example, from 1.0 to 750 mg of the active ingredient, preferably about 10 to 250 mg of the active ingredient. For parenteral administration a unit dosage may contain, for example, from 5 to 500 mg of the active ingredient, preferably about 10 to 250. Repetitive daily administration of the compounds may be desired and will vary with the condition of the patient and the mode of administration.

As used herein the term patient is taken to mean warm blooded animals, for example, birds, such as chickens and turkeys, and mammals, such as primates, humans, sheep, horses, bovine cows and bulls, pigs, dogs, cats, rats and mice.

For oral administration the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose and cornstarch. In another embodiment the compounds of general Formula 1 can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water, alcohols, oils and other acceptable organic solvents with or without the addition of a surfactant and other pharmaceutically acceptable adjuvants. Illustrative of oils which can be employed in these preparations are those of petroleum, animal, vegetable, or synthetic origin, for example, peanut oil, soybean oil and mineral oil. In general, water, saline, aqueous dextrose and related sugar solutions, ethanol and glycols such as propylene glycol or polyethylene glycol or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, a silicone rubber manufactured by the Dow-Corning Corporation.

We claim:

1. A compound of the formula

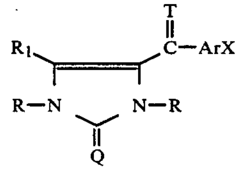

and the pharmaceutically acceptable salts thereof wherein Q and T are each oxygen or a divalent sulfur atom, R is hydrogen, lower alkanoyl, or benzoyl, $R_1$ is hydrogen or lower alkyl, Ar is phenyl, 2-, 3- or 4- pyridyl, 2- or 3- pyrryl, 2- or 3- thienyl, and 2- or 3- furanyl and X is a substituent of the group cyano, carboxy, carboxamido, alkoxycarbonyl, amidino and imidazol-2-yl.

2. A compound of claim 1 wherein Q and T are oxygen.

3. A compound of claim 2 wherein Ar is phenyl.

4. A compound of claim 2 wherein both R groups are hydrogen.

5. A compound of claim 2 wherein $R_1$ is ethyl.

6. A compound of claim 2 wherein $R_1$ is methyl.

7. A compound of claim 2 wherein X is cyano.

8. A compound of claim 2 wherein X is carboxy.

9. A compound of claim 2 wherein X is carboxamido.

10. A compound of claim 8 wherein each R is hydrogen, $R_1$ is ethyl, Ar is phenyl, said compound being 4-(4-carboxybenzoyl)-5-ethyl-1,3-dihydro-2H-imidazol-2-one.

11. A compound of claim 9 wherein each R is hydrogen, $R_1$ is ethyl, Ar is phenyl, said compound being 4-(4-carobxamidobenzoyl)-5-ethyl-1,3-dihydro-2H-imidazol-2-one.

12. A compound of claim 7 wherein Ar is phenyl, X is cyano, said compound being 4-(4-cyanobenzoyl)-5-ethyl-1,3-dihydro-2H-imidazol-2-one.

13. A method of treating cardiac failure in patient in need thereof which comprises administering to said patient a cardiotonically effective amount of a compound of claim 1.

* * * * *